United States Patent [19]

Zinser et al.

[11] Patent Number: 5,620,000

[45] Date of Patent: Apr. 15, 1997

[54] METHOD AND APPARATUS FOR MEASURING FLOW RATE, PARTICULARLY OF BLOOD

[75] Inventors: Gerhard Zinser, Speyer; Georg Michelson, Baiersdorf-Hagenau; Bernhard Schmauss, Erlangen, all of Germany

[73] Assignee: Heidelberg Engineering, Optische Messsysteme GmbH, Heidelberg, Germany

[21] Appl. No.: 510,280

[22] Filed: Aug. 2, 1995

Related U.S. Application Data

[63] Continuation of Ser. No. 267,742, Jul. 5, 1994, abandoned.

[30] Foreign Application Priority Data

Jul. 2, 1993 [DE] Germany .................. 43 22 043.6

[51] Int. Cl.$^6$ ........................................... A61B 5/026
[52] U.S. Cl. .................. 128/666; 128/691; 356/28
[58] Field of Search ...................... 128/691, 664, 128/665, 666; 356/28

[56] References Cited

U.S. PATENT DOCUMENTS

| | | |
|---|---|---|
| 4,142,796 | 3/1979 | Riva . |
| 4,743,110 | 5/1988 | Arnaud et al. ............... 356/28 |
| 4,979,818 | 12/1990 | Kobayashi ............... 128/691 |
| 5,090,416 | 2/1992 | Ogino et al. ............... 128/691 |
| 5,170,276 | 12/1992 | Zinser . |
| 5,240,006 | 8/1993 | Fujii et al. ............... 128/665 |

FOREIGN PATENT DOCUMENTS

| | | |
|---|---|---|
| 282210 | 9/1988 | European Pat. Off. . |
| 376470 | 7/1990 | European Pat. Off. . |
| 488614 | 6/1992 | European Pat. Off. . |
| 5007559 | 1/1993 | Japan ............... 128/691 |
| 9011044 | 10/1990 | WIPO ............... 128/691 |
| WO92/03084 | 3/1992 | WIPO . |
| WO93/03667 | 3/1993 | WIPO . |

OTHER PUBLICATIONS

Duteil et al., "A Double Wavelength Laser Doppler System to Investigate Skin Microcirculation," IEEE Transactions on Biomedical Engineering, vol. BME-32, No. 6, Jun. 1985, pp. 439-447.
Abstract of Published Japanese Patent No. 62-195,533.
Chehroudi et al., "A rapidly scanning . . . ", *J. Phys. E: Sci. Instrum.*, vol. 17, pp. 131-136 (1984).
Durst et al., "Laser-Doppler system . . . ", *Rev. Sci. Instrum.*, vol. 52 (11), pp. 1676-1681 (1981).

*Primary Examiner*—Angela D. Sykes
*Assistant Examiner*—Eric F. Winakur
*Attorney, Agent, or Firm*—Evenson, McKeown, Edwards & Lenahan P.L.L.C.

[57] ABSTRACT

A method for measuring the flow rate of a liquid, particularly of blood, in which the frequency shift of a laser beam reflected from the liquid is determined according to the optical Doppler effect. This method and the apparatus provided for its implementation are designed so as to enable reliable measurement of the flow rate of the flowing medium which is resolved both spatially and with respect to time. In accordance with the invention at each scanning point a number of N measured values is collected corresponding to the reflected light, N being a whole number equal to or larger than 2; the Doppler shift is calculated from the time variation of the thus measured intensity of the reflected light at the respective scanning points, and the flow rate is determined from the Doppler shift at each point of the scanning pattern.

25 Claims, 3 Drawing Sheets

METHOD AND APPARATUS FOR MEASURING FLOW RATE, PARTICULARLY OF BLOOD

This application is a continuation of application Ser. No. 08/267,742, filed on Jul. 5, 1994, now abandoned.

BACKGROUND OF THE INVENTION

This invention relates to a method for measuring the flow rate of a liquid, particularly of blood, by determining the frequency shift of a laser beam reflected in the liquid according to the optical Doppler effect. The invention also relates to an apparatus for carrying out the method of the invention.

Nilsson, Published PCT Application No. WO 93/03667 discloses a method of the above-mentioned type and an apparatus for measuring the flow rate of a liquid, particularly of blood, specifically by determining a frequency shift of a laser beam reflected in the liquid according to the optical Doppler effect. Thus, a point-type determination of the flow rate of the blood can take place by determining the frequency shift of the reflected laser beam. This measuring method is non-invasive but permits the measuring of the flow rate only at one point. In addition, high expenditures are required on the part of the patient and of the person performing the examination; particularly since the target beam has to be aimed precisely at a defined point for an extended period of time. By means of this method, it has not been possible, particularly in the field of ophthalmology, to measure the blood flow in the vascular system of the choroid membrane.

Furthermore, Riva, U.S. Pat. No. 4,142,796 discloses a process based on the optical Doppler effect as well as a corresponding apparatus for diagnostic purposes in ophthalmology.

In many fields of medical diagnostics and therapy, it is necessary to measure blood flow rates. In particular, a considerable clinical need exists in ophthalmology to carry out a locally resolved and continuous measurement of the blood flow in the retina. It is known that the three cell layers of the retina are supplied with oxygen by two independent vascular systems. The photoreceptors of the bottom layer are supplied by the choroid membrane; the bipolar cells/amacrine cells as well as the nerve cells of the top layer are supplied by the intraretinal vascular bed. It is necessary to measure the flow rates in the afferent arterioles, the retinal capillaries and in the arteriovenous shunt vessels which divert the blood flow directly into the venules while bypassing the capillaries.

In addition to the initially mentioned Doppler laser flow rate measurement, two other methods are used clinically for determining retinal blood circulation. Thus, the very frequently carried-out fluorescence angiography is based on a qualitative assessment of the retinal arterioles and capillaries after intravenous injection of a fluorescent dye. The quantitative analysis of digitized fluorescent images supplies information on special filling times, like the arm-to-retina time or the arteriovenous passage time. However, the intravenous injection of a fluorescent dye represents an invasive procedure which entails a residual risk of an anaphylactic shock and is therefore carried out predominantly in eye clinics. Fluorescence angiography is a two-dimensionally spatially resolving procedure, but it is not resolving with respect to time and is invasive with a vital residual risk.

Finally, by means of non-invasive ultrasonic Doppler sonography (duplex sonography, pulsed Doppler sonography) the blood flow rate can be determined at limited points and resolved with respect to time in orbital arteries, arterioles and venules of a diameter of up to 1 mm. In contrast, smaller vessels and capillaries of the retina cannot be detected by means of this method.

Zinser, U.S. Pat. No. 5,170,276, the disclosure of which is incorporated herein by reference, discloses an apparatus for scanning an object by means of a bundle of rays in two essentially orthogonal directions. This apparatus contains a first and a second scanner each having a mirror, whose axes of rotation extend in planes which are orthogonal with respect to one another. This apparatus has a compact construction and contains no additional optical system in the path of the rays between the above-mentioned mirrors. The mirror of the first scanner is mounted at a defined distance from its axis of rotation. An optically perfect scanning operation is ensured primarily because the center point of the mirror of the second scanner is arranged in the center of the above-mentioned distance between the axis of rotation and the mirror of the first scanner, whereby the bundle of rays passes from the mirror of the first scanner directly to the mirror of the second scanner.

Furthermore, Chehroudi et al., "A rapidly scanning laser Doppler anemometer," *J. Phys. E: Sci. Instrum.*, Vol. 17, pp 131–36 (1984) discloses a wind velocity indicator in which, while utilizing the Doppler effect and scanning by means of a laser beam, the wind velocity can be measured, for example, in a wind tunnel. Also, Durst et al., "Laser-Doppler system for rapid scanning of flow fields," *Rev. Sci. Instrum.*, Vol. 52 (11), pp 1676-81 (1981) describes a Doppler laser system by means of which primarily the wind velocity also can be measured. In apparatus or systems of this type, special rigidly arranged mirrors are provided, and such systems have, as a whole, a comparatively large space requirement. Therefore, it is not readily possible to use them in medical diagnostics and therapy.

SUMMARY OF THE INVENTION

It is the object of the present invention to provide a method which enables reliable measurement of flow rates of a flowing medium which is resolved with respect to space and time.

Another object of the invention is to provide a method for measuring flow rate which results in highly accurate measurements.

A further object of the invention is to provide an apparatus for reliably and accurately carrying out the method of the invention.

These and other objects of the invention are achieved by providing a method of measuring the flow rate of a flowing liquid from the frequency shift of a laser beam reflected from the liquid according to the optical Doppler effect, said method comprising scanning a flow area to be measured with a laser beam in a two-dimensional grid pattern of scanning points; collecting a series of N measured values representing the intensity of reflected light for each scanning point at successive time intervals, where N represents a whole number equal to or greater than 2; determining the Doppler shift of the reflected light from the time variation of the measured reflected light intensities for each scanning point; and determining the flow rate at each point of the scanning pattern from the Doppler shift.

In accordance with further aspects of the invention the objects are also achieved by providing an apparatus for measuring the flow rate of a flowing liquid from the frequency shift of a laser beam reflected from the liquid according to the optical Doppler effect, said apparatus comprising a laser scanning system comprising a laser beam source and a laser beam deflecting unit for periodically deflecting a laser beam from said source in two, mutually perpendicular directions to scan an object comprising said flowing liquid; an electronic monitoring and control system for actuating said laser scanning system and detecting the intensity of reflected laser light from said object; and a computer for analyzing the detected light intensities to obtain flow rate values for said liquid.

The method according to the invention comprises the combination of, on the one hand, the measuring of the flow rate by means of the optical Doppler effect and, on the other hand, the laser scanning technique, whereby by means of the design of the scanning operation and the highly sensitive detection, the required measuring range is covered and the required measuring accuracy is achieved. In contrast to the known methods, the measurement of the flow rate of the liquid takes place in a simultaneously three-dimensional manner, resolved locally and with respect to time, and is non-invasive and fast. The object to be examined, such as the retina, is scanned by the laser beam in a two-dimensional grid-shaped manner, whereby at every point the reflected light is measured several times in rapid succession by a repeated scanning. The Doppler shift is calculated from the time variation of the measured intensity of the light reflected at the respective scanning point and, the flow rate, particularly of the blood, is determined at every point from the calculated Doppler shift. An image of the retinal blood flow is obtained which is locally resolved in two dimensions. In addition, by repeating the described measurement, an image of the retinal blood flow is obtained which is resolved with respect to time. Through implementation of the laser scanning system, particularly in a confocal arrangement, a local resolution as to depth is also obtained so that the measurements may be made selectively in individual layers of the object. By appropriately choosing the wavelength of the laser, the intraretinal vascular bed and the vessels of the choroid may thus be measured separately from one another during the examination of the retina.

The scanning Doppler laser flow rate measurement method can therefore be used outside as well as within the medical field. Basically, the range of application of the method extends over all fields which require a spatially resolved measurement of the flow rate of a flowing medium. In ophthalmology the method of the invention can be used in all areas in which invasive fluorescence angiography is used today and can replace it. The method is non-invasive and requires no dilating of the pupil of the examined eye. In addition, the method enables measurement of the retinal blood flow which is resolved with respect to time as well as in a three-dimensional local manner. Other typical applications of the method include measurements of the regulating capacity of the retinal vascular system as well as determination of retinal blood flow conditions in glaucoma. Medical applications outside ophthalmology include in the first instance the locally resolved blood flow-determination of the skin as well as other organs, such as the heart, the liver, the intestine and the brain, during operations.

The apparatus for carrying out the method according to the invention comprises a laser scanning system, an electronic monitoring and control system for the scanning operation and for collecting the scanning data, and a computer for analyzing the collected data. The laser scanning system comprises a laser source, a beam deflecting unit for periodically deflecting the laser beam in two directions which are perpendicular with respect to one another, and an imaging optical system for imaging the scanning laser beam on the object to be examined. Also, a focussing element is provided for moving the focal plane, a decoupling element for separating the reflected light beam from the illuminating laser beam, and a detector for measuring the intensity of the reflected light beam. In ophthalmology, when the retina is examined, the light-refracting components of the eye itself are part of the imaging optical system by means of which the scanning laser beam is imaged on the object to be examined. The above-mentioned beam deflecting unit as well as the focussing element may be constructed in particular as a device for scanning an object as described in U.S. Pat. No. 5,170,276, the disclosure of which is incorporated herein by reference.

DETAILED DESCRIPTION OF THE DRAWINGS

The invention will be described in further detail hereinafter with reference to illustrative preferred embodiments shown in the accompanying drawings in which.

DETAILED DESCRIPTION OF PREFERRED EMBODIMENTS

Figure 1:
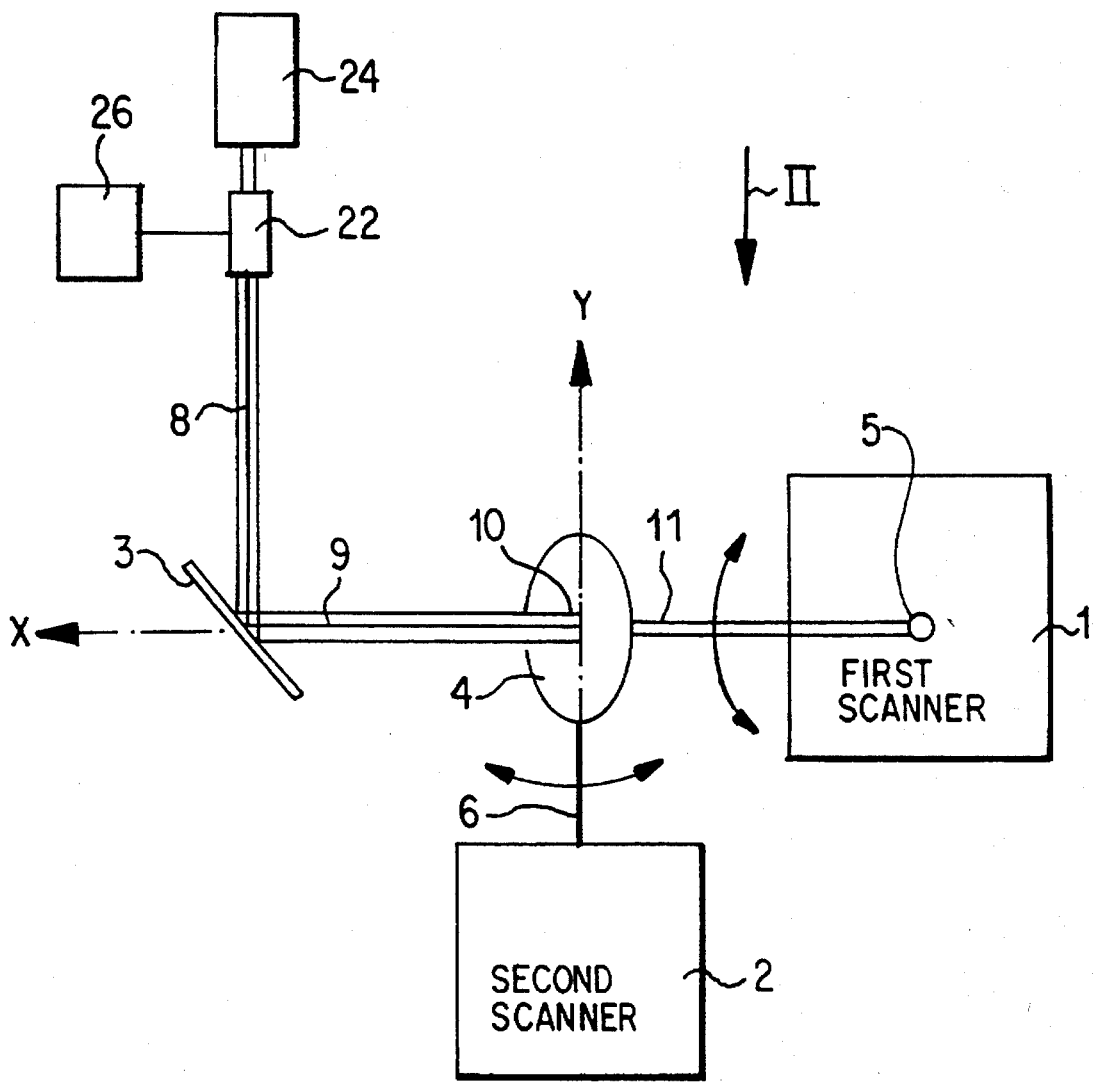
FIG. 1 is a schematic diagram of an apparatus for carrying out the method of the invention.

FIG. 1 schematically illustrates a first scanner 1 and a second scanner 2. A first mirror 3 is mechanically coupled with the first scanner 1 and is arranged so that it can be swivelled about an axis 5 which is perpendicular to the plane of the drawing. A second mirror 4 is associated with the second scanner 2 and can be swivelled about an axis 6 which is in parallel to the plane of the drawing. The axes 5 and 6 extend in mutually orthogonal planes and are perpendicular to one another. It is important that the first mirror 3 is arranged at a distance 7 with respect to the scanner 1, and that the axis of rotation 6 of the scanner 2 and mirror 4 extends in the center between the axis of rotation of scanner 1 and mirror 3. In accordance with the invention, the center of the second mirror 4 is positioned at the midpoint between the center of the first mirror 3 and the axis of rotation 5 of the scanner 1 and mirror 3. The axis of rotation 5 of scanner 1 and first mirror 3 extends essentially parallel to the plane of the mirror, in which case, however, the distance 7 exists between the center of the first mirror 3 and the axis of rotation 5. The axis of rotation 6 of scanner 2 and second mirror 4 also extends essentially in parallel to it. The axis of rotation 6 also essentially extends through the center of the second mirror, in which case, however, a predetermined spacing may be provided, as required. It is important that the center of the second mirror is arranged at half the distance 7 from the axis of rotation 5.

There are no lenses or optical imaging devices between the two mirrors 3 and 4, and thus, the beams 9 inside the apparatus travel directly from one mirror to the other. Beams 8 are illustrated schematically which travel from or to a device 22 for the decoupling the beams. The beams from a beam source 24, particularly a laser, arrive first at the decoupler, and from there pass to the apparatus according to FIG. 1, and farther to the object. The beams reflected by the object pass again through the apparatus according to the invention and from there travel to the decoupler 22, which then directs them to the analysis device or detector 26, preferably an avalanche photodiode, for further analysis. The beams 10 directed toward the object or reflected from the object extend essentially orthogonally to the plane in which the beams 8 and 9 extend.

It is assumed that an orthogonal system of coordinates is situated with its point of origin in the center of the second mirror 4, the X-Y-plane coinciding with the plane of the drawing. Beams 8 extend parallel to the Y-direction, while beams 9 extend between the two mirrors 3, 4 along the X-direction. The axis of rotation 6 of the second scanner is in the Y-direction, while the axis of rotation 5 is orthogonal with respect to the X-Y plane.

Figure 2:
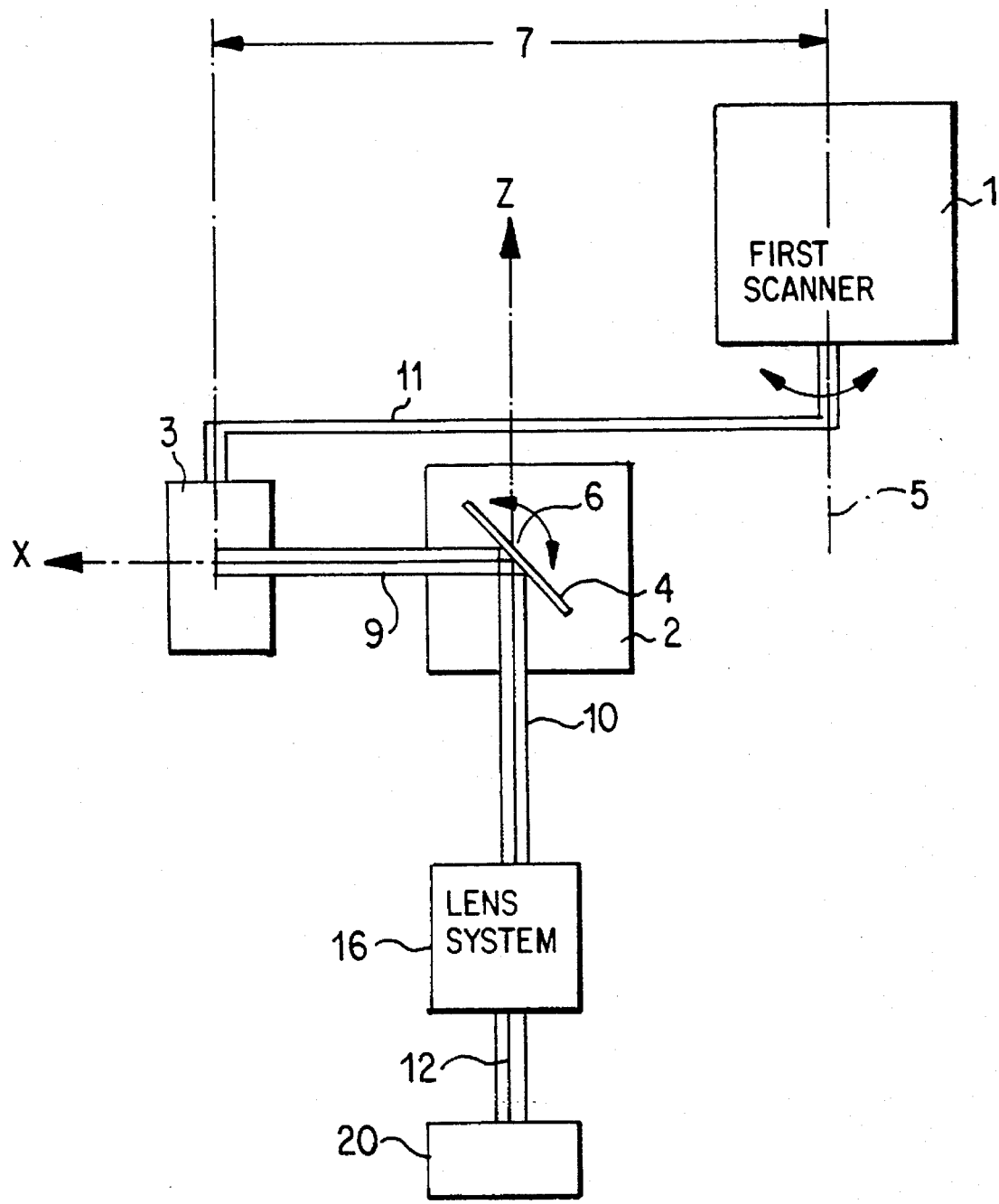
FIG. 2 is a schematic diagram of the apparatus of FIG. 1 viewed in the direction of arrow II.

FIG. 2 is a view of the apparatus of FIG. 1 in the viewing direction II, the axis 5 extending in the plane of the drawing, and the axis 6 extending perpendicularly to the plane of the drawing. The mirror 3 is connected with the scanner 1 by way of an arm 11 and therefore is spaced a distance 7 from the axis of rotation 5. The plane of the drawing corresponds to the X-Z plane of the system of coordinates with the origin in the center of the second mirror 4. The beams 10 which are reflected by the second mirror 4 or returned by the object to the mirror 4 extend in the Z-direction. The axis of rotation or the pivot of the second mirror 4 or the second scanner 2 is positioned in the center between the axis of rotation 5 and the pivot of the mirror 3. Also shown are the beams 10 which are directed by the mirror 4 through an imaging lens system or a focussing element 16 along an optical axis 12 to the object 20 and reflected back again. The beams 8 which travel from the decoupler to the mirror 3 of the first scanner and are reflected by it extend orthogonally forward in front of the plane of the drawing.

The beams reflected by the mirror 4 pass through the focussing element 16 along the optical axis 12 to the object 20, whereby the illuminating laser beam is deflected in two dimensions perpendicularly to the optical axis 12 because of the periodic and synchronous movement of the two mirrors 3 and 4. Although the described apparatus is used in a particularly advantageous manner for implementing the method of the invention because it assures a correct imaging of the object using a compact construction, other laser scanning systems may also be used within the scope of the invention.

Figure 3:
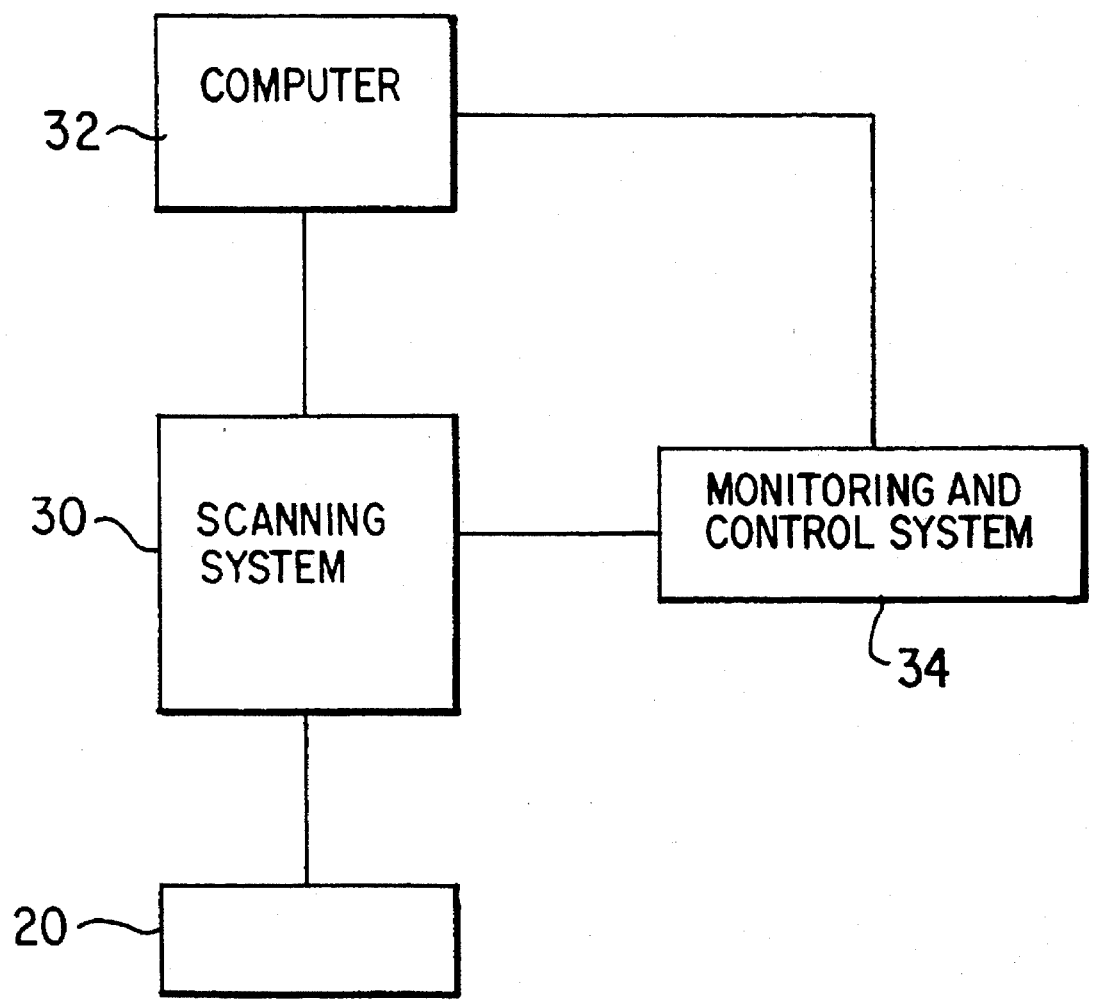
FIG. 3 is a schematic diagram of the basic construction of the apparatus according to the invention.

FIG. 3 illustrates the basic construction of the apparatus according to the invention with the laser scanning system 30 which is operated by means of a computer 32 and an electronic monitoring and control system 34. In order to explain the relationships, reference will be made in the following to the components of the apparatus of FIGS. 1 and 2. The second mirror 4 oscillates at a high frequency f and moves the laser beam along a line of the scanned object. The intensity of the light reflected during the scanning is measured by the detector 26 at fixed time intervals so that a series of M-measured values is obtained along the scanned line which represent the reflected light intensities at M-individual points along this scanned line. These M-measured values are digitized and stored in the computer 32. The scanning along this first line of the object is repeated successively N-times so that each of the M-points along the line is measured N times at equal time intervals of 1/f. Thus, a matrix is collected of M×N measured values. This location-time matrix contains in each of its N-lines in a locally resolved manner and in each of its M-columns in a manner resolved with respect to time the reflected light intensity at the individual points along the scanned first line of the object.

After capturing the location-time matrix for the one first line of the object, the scanning laser beam is shifted by means of the first mirror 3 of the beam deflecting unit perpendicularly to the direction of the scanned line to an adjacent second line of the object. The above-described measuring operation is repeated for this second line. Subsequently, in a corresponding manner, additional parallel lines of the object are scanned, and, for L-lines a corresponding number of L matrices are obtained, each with M×N measured values. Consequently, in accordance with the invention, a two-dimensional field of the object is scanned at M×L points, and for each of these points a sequence of N measured values exists at identical time intervals. By means of this series of spatial scanning operations, on the one hand, and time-related scanning operations, on the other hand, which are important for the invention, it is possible to cover the required range of the flow rate and to use efficient numerical processes for the spectral analysis. The high scanning speed results in a very high efficiency during the detection of the reflected light, particularly by means of a highly sensitive detector. The optical construction of the scanning system, which is illustrated in FIGS. 1 and 2, assures a high light yield, primarily because of the small number of optical components, and also the highly sensitive detection, which is effected particularly by means of an avalanche photodiode.

In a typical embodiment for measuring the retinal blood flow, for example, the following operating parameters may be used:

The second mirror 4 for the scanning of a line along the retina oscillates at a frequency f=8,000 Hz. The factors M, N and L each have the value 256. As explained above, a field of L=256 lines at M=256 points on each line is scanned on the object. If by means of the imaging lens system of the focussing element, the length of the scanned lines is selected to be substantially 3 mm, then the adjacent spacing between two measuring points along a line as well as between two adjacent lines on the retina will be about 0.01 mm. The spatial resolution of the measurement is determined by this value. The intensity of the reflected light is measured at each point in the line at fixed intervals of 1/f=0.000125 seconds. The data acquisition time for the location-time matrix of a line thus amounts to 1/f×L=0.032 seconds, and consequently, the overall acquisition time is 8 seconds at the operating values discussed above. Overall, for the typical measurement embodiment described above, 256×256×256 measured values are collected and digitized.

In order to evaluate the correspondingly collected and digitized data, it is assumed that at every point of the examined object, a portion of the measured light is reflected by movable components of the object, particularly the constituents of the flowing blood, and another portion is reflected by stationary parts of the object. Because of the Doppler effect, the frequency of the light reflected from the moving parts shifts relative to the frequency of the light reflected from the stationary parts. Because of the coherence of the laser light, the superposition and interference of these two components result in time fluctuations in the intensity of the reflected light from one point of the object measured at the detector.

In accordance with the foregoing description, the variations over time in the intensity reflected from a single point are contained in a column of the location-time matrix which corresponds to this point. Analysis of the time fluctuations leads to the calculation of the flow rate at this point which causes them. For this purpose, each column of the matrix of measured values is subjected in accordance with the invention to a frequency analysis, such as, for example, the known discrete Fourier transform, from which the frequency distribution of the time fluctuation of the reflected light intensity is determined. Since a given flow rate results in a fluctuation in intensity of the measured light having a specific frequency, the speed of the moving component at the respective point of the object can be determined from the frequency distribution. Within the scope of the invention, the discrete Fourier transform of the measured values can be carried out by means of software or by means of special hardware of the computer.

Following the above-described determination of the typical flow rate at each point of the scanned two-dimensional field of the object, a matrix of M×L flow rates is obtained. This matrix can be displayed, for example on the screen of the aforementioned computer, particularly as an image which represents the flow rate in a locally resolved manner. For the typical embodiment described above and the operating parameters given above, the following limits for the measurement of the flow rate are obtained:

The limiting frequency for the discrete Fourier transform is f/2; i.e. 4,000 Hz in the described embodiment. An object which moves at a velocity v along the direction of propagation of the light, i.e. parallel to the optical axis, causes a frequency shift of the reflected light and thus a modulation of the measured light intensity at a frequency $F=2\ v/\lambda$ wherein $\lambda$ corresponds to the light wavelength. Thus, with the aforementioned operating parameters, a maximum flow rate of 2 mm/s can be measured.

Special embodiments of the method and/or apparatus according to the invention will now be described. Thus, the laser scanning system may be constructed particularly as a confocal optical system, in which case the detector for the reflected light is constructed in a known manner essentially in point form. For this purpose, for example, a small diaphragm is arranged in front of the detector, disposed in a position which is optically conjugated with respect to the focal plane of the scanning system. This assures that substantially only that light is detected which is reflected from a small area around the respective predetermined focal plane. In contrast, light reflected or scattered at other points is effectively suppressed because of the confocal construction. A high optical resolution of the system is achieved not only perpendicular to the optical axis but also in parallel to it. Thus, it is possible to measure the flow rate selectively in individual layers of the object, for example, at the vascular system of the retina, and, in addition, the flow rates in the retinal vascular bed as well as the vascular system of the choroid can be represented separately from one another and in a three-dimensional manner.

In a further specific embodiment, the optical system is designed to be polarization-sensitive. For this purpose, a linearly polarized laser source, particularly a laser diode, is used, or unpolarized laser light is linearly polarized by means of a polarizer. The device 22, which according to FIG. 1 is provided for decoupling, is also constructed to be polarization-sensitive such that only reflected light which is linearly polarized in a direction which is rotated by 90° with respect to the illuminating beam reaches the detector 26. In such an arrangement, the detection of the light which is directly reflected by the object while maintaining the polarization direction is effectively suppressed and substantially only scattered light is detected. Alternatively, by means of a quarter-wave plate which is arranged at a point of the beam path between the examined object 20 and the decoupler 22, the polarization direction of the reflected light is rotated by 90° compared to the polarization direction of the laser source. Consequently, in conjunction with the polarization-sensitive decoupler 22, essentially the light is detected which was reflected from the object 20 while maintaining the polarization direction. By selecting the scattered light, on the one hand, or the directly reflected light, on the other hand, further information is obtained concerning the distribution of the flow rate.

In another embodiment of the invention, the variation of the wavelength of the laser light is utilized, specifically by the installation of two different lasers in the apparatus, whereby it becomes possible to scan different areas of the vascular system. It is thereby assumed that light of a different wavelengths will penetrate the retinal tissue to different depths. The retinal pigment epithelium, which separates the retinal vascular system from the choroid vascular bed, is not transparent to visible light but is transparent to infrared light. If visible laser light is used in accordance with the invention, light is reflected only by the tissue above the retinal pigment epithelium, and the blood flow is measured selectively in the retinal vascular system. In contrast, if light in the near infrared range is used, the vascular bed with the choroid is also reached, and the measured flow rate is a superposition of the blood flow in the retina and the blood flow in the choroid. By subtracting the blood flow image obtained with visible light from that obtained with infrared light according to the invention, the blood flow of the choroid alone is obtained. In addition, depth localization is achieved with the confocal construction described above.

Finally, it should be noted that the measurement of flow rates over time according to the invention also makes it possible to detect time variations in the flow rates in the vascular system.

By synchronizing the data acquisition with the heart rate and representing the retinal blood flow in a time-resolved manner over the course of several heartbeats, the course of the speed of the pressure wave from each heartbeat (pulse wave) within the retinal vascular system can be measured in a particularly advantageous manner. Thus, heterogeneities of the pulse wave propagation and/or of the vascular resistance can be detected in a reliable manner.

Basically, a polygonal mirror or an oscillating rotating mirror can be used as the second, rapidly moving mirror of the beam deflecting unit (mirror 4 according to FIG. 1) in which case this mirror moves the laser beam along a line over the object. With an oscillating pivotable mirror, after each scanning movement of the mirror in order to scan an object line, there is a dead time for return movement of the mirror to its starting position. In accordance with the invention, the return travel time of the mirror is also used for acquiring data. As a result, for each scanned line of the object, a second location-time matrix of M×N measured values is obtained which is time-shifted with respect to the first location-time matrix. These two location-time matrices are subjected to the Fourier transform separately from each other and subsequently combined, while taking into account the displacement of the Fourier transform, to an overall spectrum. This specific embodiment improves the signal-to-noise ratio.

In order to evaluate the frequency spectra, which result from the Fourier transform of the location-time matrices, different alternative arrangements may be used within the scope of the invention. The detection of the characteristic limit frequency, which exists in the case of a strong flow, permits the measurement of the highest occurring flow velocity. The determination of the center of gravity of the frequency spectrum or the determination of the frequency whose spectral power density value corresponds to the arithmetic mean of the overall spectrum enables the average flow rate to be determined. In addition, comparison of the spectral power densities of individual frequencies enables the relative frequency of different flow rates to be determined.

One particular type of analysis of the frequency spectra is the band pass method. In this method, the mean value of the spectral power density in a specific frequency interval is calculated, which corresponds to a specific average flow rate, and a blood flow image of this particular flow rate range is generated from this average flow rate. By selecting different center frequencies of such band passes, slow flows, for example capillary flows, and fast flows, for example arteriolar flows, can be examined in a targeted manner. In this case, the spectral width of the pass range of the band passes is a measure of the respective detected frequency range and also the flow rate range.

In accordance with a further embodiment of the invention, the described apparatus and/or method for Doppler laser flowmetry can be used. In this further embodiment, the measured flow rate at each point of the examined area is multiplied by the ratio of the light intensities reflected by moving and stationary components, which is obtained from the analysis of the frequency spectra. In this way a locally resolved image of the overall flow is obtained in a particularly advantageous manner.

The foregoing description and examples have been set forth merely to illustrate the invention and are not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A method of measuring a flow rate of a flowing liquid from a frequency shift of a laser beam reflected from the liquid according to an optical Doppler effect, said method comprising:

scanning a flow area to be measured with a laser beam in a two-dimensional grid pattern of M×L scanning points, where M and L each represent a whole number, said scanning being carried out by scanning a series of M individual scanning points along a first scan line and measuring an intensity of reflected light from each of said series of M scanning points, whereby M measured values are detected and stored, and repeating the scanning along said first scan line N times, whereby a series of N measured values representing an intensity of reflected light is collected for each of said M scanning points at successive time intervals, where N represents a whole number equal to or greater than 2, and thereafter successively scanning in the same manner as said first scan line, a series of (L-1) additional scan lines parallel to said first scan line;

determining a frequency shift of the reflected light due to the Doppler effect from a time variation of the measured reflected light intensities for each of said M×L scanning points; and determining the flow rate of each of said M×L points of the scanning pattern from the frequency shift.

2. A method according to claim 1, wherein said liquid is blood flowing in blood vessels of living tissue.

3. A method according to claim 2, wherein the detection of the measured reflected light intensity values is synchronized with a heart beat.

4. A method according to claim 1, wherein said scanning is carried out in at least two different focal planes at different depths in a scanned object.

5. A method according to claim 4, wherein said scanning in at least two different focal planes is effected using a laser scanning system in a confocal arrangement.

6. A method according to claim 1, wherein different wavelengths of laser light are selected for scanning different areas of an object being examined.

7. A method according to claim 6, wherein different wavelengths of laser light are selected by selecting among a plurality of laser light sources which emit different wavelengths of laser light.

8. A method according to claims 1, wherein a matrix of M×N measured values is collected for each scan line, each said matrix containing N rows of spatially-resolved reflected light intensity values and M columns of time-resolved reflected light intensity values, further comprising spectrally analyzing the measured time-resolved reflected light intensity values for at least one scan point; determining the frequency distribution of fluctuations in the time resolved reflected light intensity values for said scan point, and determining the flow rate distribution of moving components of the scanned flow at said scan point from the previously determined frequency distribution.

9. A method according to claim 8, wherein the measured time-resolved reflected light intensity values are spectrally analyzed by subjecting them to a discrete Fourier transform.

10. A method according to claim 1, wherein during said scanning, where M and L represent integers greater than 2, displaying the M×L flow rate values in the form of a visible representation to obtain a spatially resolved flow rate image.

11. An apparatus for measuring a flow rate of a flowing liquid from a frequency shift of a laser beam reflected from the liquid according to an optical Doppler effect, said apparatus comprising a laser scanning system comprising a laser beam source and a laser beam deflecting unit for periodically deflecting a laser beam from said source in two, mutually perpendicular directions to scan an object comprising said flowing liquid;

an electronic monitoring and control system for actuating said laser scanning system to scan a flow area of the object to be measured in a two-dimensional grid pattern of M×L scan points, where M and L each represent a whole number, said monitoring and control system actuating said laser scanning system to scan a series of M individual scan points along a first scan line and measure an intensity of reflected laser light from each of said series of M scan points, whereby a series of M measured values are detected and stored, and repeat the scan along said first scan line N times, where N represents a whole number equal to or greater than 2, whereby a series of N measured values representing the intensity of reflected light is collected for each of said M scan points, and thereafter successively scan in the same manner as said first scan line, a series of (L-1) additional scan lines parallel to said first scan line; and a computer for analyzing the detected light intensities to obtain flow rate values for said liquid.

12. An apparatus according to claim 11, wherein said laser scanning system comprises an imaging lens system for imaging the scanning laser beam on said object.

13. An apparatus according to claim 11, wherein said laser scanning system comprises a focussing element for adjustably focussing said laser scanning system in a desired focal plane.

14. An apparatus according to claim 11, wherein said beam deflecting unit comprises first and second periodically and synchronously moved mirrors for deflecting said laser beam in two dimensions orthogonal to an optical axis leading from said laser scanning system to said object to be scanned.

15. An apparatus according to claim 14, wherein said second mirror oscillates at a frequency (f) and deflects said laser beam N times, along each of said scan lines on the object to be scanned at equal time intervals of 1/f; said monitoring and control system measuring the reflected light intensity at a series of M points along each of said scan lines each time said laser beam is deflected along said scan line, whereby sets of M×N measured reflected light intensity values are obtained.

16. An apparatus according to claim 15, further comprising means for digitizing said M×N measured values and electronically storing the digitized values in a matrix of N lines and M columns, whereby the stored values in each of said N lines of the matrix represent the reflected light intensity along said first scan line in a spatially resolved manner, and the stored values in each of said M columns of the matrix represent the reflected light intensity at an individual scanning point in a time-resolved manner.

17. An apparatus according to claim 15, wherein said second mirror deflects said laser beam from a scan start point at one end of said scan line to a scan end point at an opposite end of said scan line and then returns said laser beam to said start point during a return time, and wherein said apparatus also collects scanning data during said return time, whereby a second set of measured reflected light intensity values is obtained for said scan line which is displaced in time with respect to said first set; said computer comprising means for subjecting said first and second sets of measured light intensity values separately to Fourier transform analysis and subsequently combining results obtained in the separate analyses into an overall spectrum while taking into account the time displacement to obtain an overall spectrum, whereby an improved signal-to-noise ratio is obtained for the measured flow rate.

18. An apparatus according to claim 14, wherein said first mirror is pivotable about an axis of rotation spaced a distance from said first mirror, and said second mirror has a center point arranged midway between said first mirror and the axis of rotation of said first mirror; and wherein laser beams pass directly between said first and second mirrors without traversing any other optical elements.

19. An apparatus according to claim 14, wherein said first mirror is coupled via an arm with an associated axis of rotation spaced a distance from the first mirror, said arm having a length substantially corresponding to the distance between said first mirror and the associated axis of rotation.

20. An apparatus according to claim 11, wherein said computer comprises means for subjecting detected reflected light intensity values to Fourier transform analysis.

21. An apparatus according to claim 11, wherein said monitoring and control system comprises an avalanche photodiode for detecting the intensity of reflected laser light from a scanned object.

22. An apparatus according to claim 11, wherein said laser beam source comprises a linearly polarized laser source or an unpolarized laser source directed through a polarizing filter, whereby said laser beam source produces a beam of linearly polarized laser light which is used to scan the object to be scanned.

23. An apparatus according to claim 22, wherein said monitoring and control system comprises a polarization-sensitive decoupler which receives reflected laser light from said scanner and transmits to a detector only reflected light which is linearly polarized in a direction rotated 90° with respect to the polarized light beam used to scan the object to be scanned.

24. An apparatus according to claim 22, wherein said monitoring and control system comprises a polarization-sensitive decoupler which receives reflected laser light from said scanner and a quarter-wave plate arranged between the object to be scanned and the decoupler such that reflected polarized light has a direction of polarization rotated 90° relative to the polarized light beam used to scan the object to be scanned.

25. An apparatus according to claim 11, wherein said computer comprises means for resolving a frequency spectrum of detected reflected light into a first intensity value due to reflection from moving components of the flowing liquid and a second intensity value due to reflection from stationary components of the object to be scanned, and the measured flow rate at each point of a scanned area of the object to be scanned is multiplied by a ratio of the light intensity reflected from stationary components of the object to the light intensity reflected from moving components of the flowing liquid.

* * * * *